US00PP25376P3

(12) United States Plant Patent
Skotak, Jr.

(10) Patent No.: US PP25,376 P3
(45) Date of Patent: Mar. 24, 2015

(54) ***GUZMANIA* PLANT NAMED 'G9518'**

(50) Latin Name: *Guzmania conifera×ligulata*
Varietal Denomination: G9518

(71) Applicant: Chester Skotak, Jr., Alajuela (CR)

(72) Inventor: Chester Skotak, Jr., Alajuela (CR)

( * ) Notice: Subject to any disclaimer, the term of this patent is extended or adjusted under 35 U.S.C. 154(b) by 122 days.

(21) Appl. No.: 13/986,066

(22) Filed: Mar. 27, 2013

(65) Prior Publication Data

US 2014/0298554 P1 Oct. 2, 2014

(51) Int. Cl.
*A01H 5/00* (2006.01)

(52) U.S. Cl.
USPC ..... Plt./371

(58) Field of Classification Search
USPC ..... Plt./371
See application file for complete search history.

*Primary Examiner* — Anne Grunberg

(57) ABSTRACT

A new and distinct *Guzmania* cultivar named 'G9518' is disclosed, characterized by a very durable plant with a uniquely shaped inflorescence and white tipped flowers. The new variety is a *Guzmania,* typically produced as an indoor ornamental plant.

1 Drawing Sheet

Latin name of the genus and species: *Guzmania conifera× lingulata.*

Variety denomination: 'G9518'.

BACKGROUND OF THE INVENTION

The new cultivar is a product of a planned breeding program. The objectives of the planned breeding program were to develop new *Guzmania* varieties. The new variety originated from a cross pollination of the seed parent, unpatented *Guzmania conifera×lingulata* variety 'Cardinalis' and the pollen parent, the unpatented *Guzmania lingulata* variety 'El Cope'. The crossing was made during September of 2002 in a commercial greenhouse in Alajuela, Costa Rica.

The new variety was discovered by the inventor, Chester Skotak Jr., in September of 2006 in a group of seedlings resulting from the crossing. The new cultivar was found in a commercial greenhouse in Alajuela, Costa Rica.

Asexual reproduction of the new cultivar 'G9518' was first performed at a commercial laboratory in Evergem, Belgium, by tissue culture on August of 2011. Subsequent propagation by tissue culture has shown that the unique features of this cultivar are stable and reproduced true to type.

SUMMARY OF THE INVENTION

The cultivar 'G9518' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'G9518'. These characteristics in combination distinguish 'G9518' as a new and distinct *Guzmania* cultivar:

1. Unique inflorescence shape.
2. Very durable plants, resistant to various environmental and physical stressors.
3. White tipped flowers

PARENT COMPARISON

Plants of the new cultivar 'G9518' are similar to plants of the seed parent, the unpatented variety of *Guzmania* know as 'Cardinalis' in most horticultural characteristics, however, plants of the new cultivar 'G9518' produces different shaped inflorescence compared to that of the seed parent 'Cardinalis'.

Plants of the new cultivar 'G9518' are similar to the pollen parent, the unpatented, variety of *Guzmania* know as 'El Cope' in most horticultural characteristics. However plants of the new cultivar 'G9518' produce a different flower shape compared to the flower shape of pollen parent 'El Cope', which is wider and rounder in shape. Additionally the leaves produced by the new cultivar 'G9518' are narrower and shinier than those of pollen parent 'El cope'. Finally the leaves produced by the new cultivar 'G9518' are green on top and on the underside, whereas the leaves of pollen parent 'El Cope' are a darker red-brown on the underside.

COMMERCIAL COMPARISON

Pollen parent variety is the best commercial comparison known to the inventor.

BRIEF DESCRIPTION OF THE PHOTOGRAPH

The accompanying photograph in FIG. 1 illustrates in full color a typical plant of 'G9518' grown in a greenhouse in Evergem, Belgium. This plant is approximately 18 months old, shown in an 11 cm. pot. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'G9518' plants grown in a climate controlled greenhouse in Evergem, Belgium. Temperatures ranged from 18° C. to 22° C. at night to 20° C. to 28° C. during the day. No artificial light, photoperiodic or chemical treatments were given to the plants. Measurements and numerical values represent averages of typical plant types.

Botanical classification: *Guzmania coniferax×lingulata* 'G9518'.

Variety denomination/filing name: 'G9518'.

PROPAGATION

First propagation method: Tissue culture.

Type of propagation typically used: Tissue culture.

Time to initiate roots: About 15 days at approximately 20° C.

Time to produce a rooted cutting/liner: About 180 days at approximately 22° C.

Root description: Moderately dense, moderately branched, fine, fibrous, not fleshy, colored near Grey RHS 201A and 201B.

PLANT

Growth habit: Upright, monopodial.

Height: Average: 26.9 cm.

Plant spread: Average: 52.2 cm.

Normal pot size: 11 cm.

Growth rate: Moderate.

Branching characteristics: Monopodial, leaves form a basal rosette, inflorescence grows from the center of the rosette.

Number of leaves per scape: Average: 23.

Stem length: No stems present, scape grows directly from rosette.

FOLIAGE:

Leaf:

*Arrangement.*—Rosulate; leaves (average: 23) placed in a basal Rosette.

*Average length.*—Approximately 32.5 cm.

*Average width.*—Approximately 4.4 cm.

*Shape of blade.*—Ligulate.

*Aspect.*—Arching downward.

*Apex.*—Apiculate, curved downward.

*Base.*—Sheathing. Sheath length: Average 7.2 cm. Sheath width: Average 7.5 cm. Sheath color: Greyed-green, near RHS 197A.

*Margin.*—Entire.

*Texture of top surface.*—Smooth, glossy.

*Texture of bottom surface.*—Smooth, moderately glossy.

*Color.*—Young foliage upper side: Green to yellow-green; in between near RHS 137A and 147A, closest to RHS 137A. Young foliage under side: Yellow-green; a color in between near RHS 146A and 147B. Mature foliage upper side: Green to yellow-green; in between near RHS 137A and 147A, closest to RHS 137A. Mature foliage under side: Yellow-green; near RHS 147A, towards the base strongly tinged greyed-orange; near RHS 177A.

*Venation.*—Type: Parallel. Venation coloration: Upper side: Indistinguishable from leaf blade. Under side: Indistinguishable from leaf blade.

INFLORESCENCE

General description:

*Inflorescence height, excluding scape.*—Approximately 6.8 cm.

*Inflorescence width.*—Approximately 14.4 cm.

Scape:

*Length.*—Approximately 20.1 cm.

*Width.*—Approximately 1.3 cm.

*Aspect.*—Approximately 90° angle to rosette (near vertical).

*Strength.*—Very strong.

*Color.*—Yellow-green, near RHS 150D.

Bracts:

*Scape/lowermost bracts.*—Shape: Ligulate. Length: Approximately 14.9 cm (excluding sheath). Width: Approximately 2.9 cm. Quantity: Average 10. Tip: Long apiculate. Base: Sheathing. Sheath length: Approximately 4.0 cm. Sheath width: Approximately 4.0 cm. Sheath color: Greyed-yellow; near RHS 161A. Margin: Entire. Color upperside: Upper half Green to yellow-green; in between near RHS 137A and 147A, closest to RHS 137A, lower half moderately to heavily tinged greyed-red; near RHS 179A to 179B. Uppermost scape bracts red; near RHS 44A, outer tip greyed-purple; near RHS N186C. Color underside: Greyed-red; near RHS 178A but darker, tip yellow-green; near RHS 147A. Uppermost scape bracts red; near RHS 42A, outer tip greyed-purple; near RHS N186C.

*Terminal bracts.*—Shape: Short ligulate. Length: Approximately 5.9 cm (incl. sheath). Width: Approximately 1.7 cm. Quantity: Average 45. Tip: Bluntly acute to obtuse. Base: Sheathing. Sheath length: Approximately 1.8 cm. Sheath width: Approximately 1.8 cm. Sheath color: White; near RHS 155C. Margin: Entire. Coloration Terminal Bracts: Upperside: Red, near RHS 44A, apex white, near RHS NN155C. Underside: Red; near RHS 42A, apex white, near RHS NN155C.

OTHER CHARACTERISTICS

Disease resistance: Normal.

Drought tolerance and cold tolerance: Normal.

Fruit/seed production: No production observed to date.

What is claimed is:

1. A new and distinct cultivar of *Guzmania* plant named 'G9518' as herein illustrated and described.

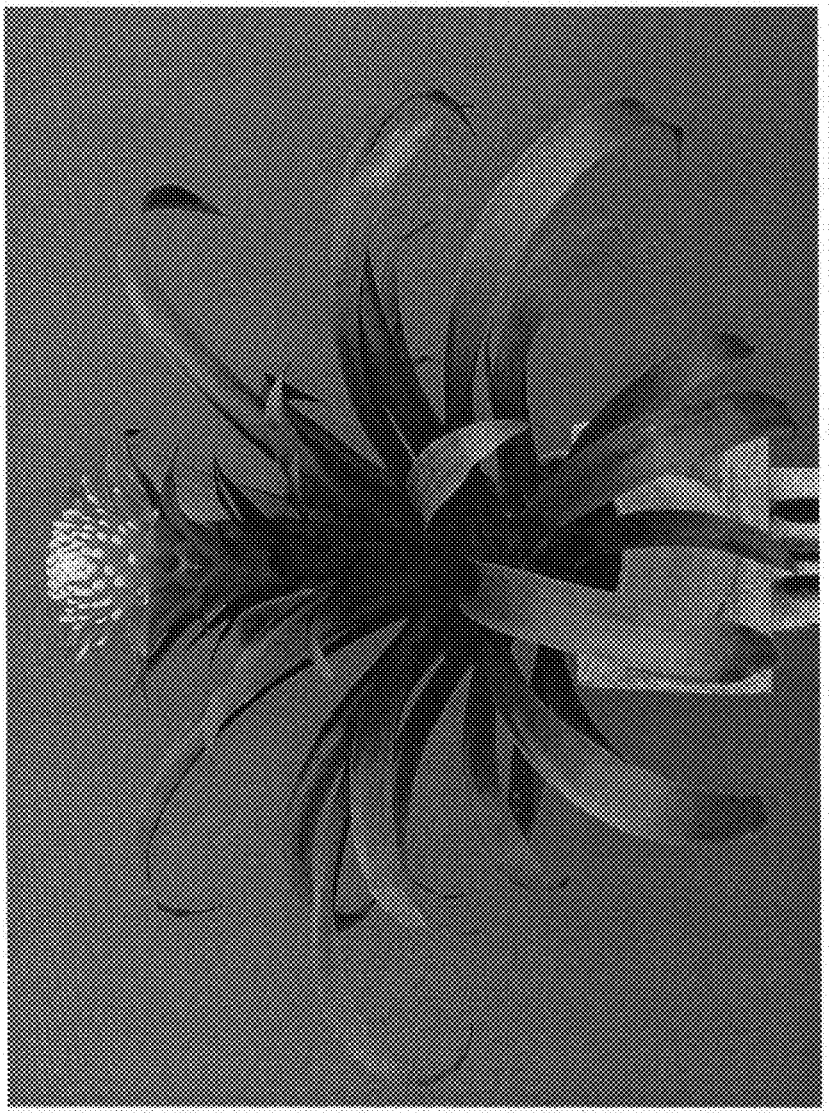

* * * * *